United States Patent [19]

Yasuda et al.

[11] 4,415,876
[45] Nov. 15, 1983

[54] GAS SENSOR

[75] Inventors: Eturo Yasuda; Mitsuru Asano; Minoru Ohta, all of Okazaki, Japan

[73] Assignee: Nippon Soken, Inc., Nishio, Japan

[21] Appl. No.: 227,780

[22] Filed: Jan. 23, 1981

[30] Foreign Application Priority Data

Jan. 25, 1980 [JP] Japan .................................. 55-8200

[51] Int. Cl.³ ........................ G01N 27/12; H01C 1/02
[52] U.S. Cl. ............................................ 338/34; 73/23
[58] Field of Search ............... 73/23 R, 27 R; 338/34; 324/65 CR

[56]     References Cited
         U.S. PATENT DOCUMENTS

| 3,599,090 | 8/1971 | Fitzpatrick | 324/65 CR |
| 3,959,765 | 5/1976 | Stewart | 338/34 |
| 4,130,797 | 12/1978 | Hattori et al. | 324/65 R |
| 4,151,503 | 4/1979 | Cermack et al. | 338/14 |
| 4,193,289 | 3/1980 | Springer et al. | 73/27 R |
| 4,206,173 | 6/1980 | Yamaguche et al. | 73/27 R |
| 4,225,842 | 9/1980 | Schlesselman et al. | 338/34 |
| 4,287,751 | 9/1981 | Yasuda et al. | 73/23 |
| 4,288,774 | 9/1981 | Takami et al. | 338/34 |
| 4,308,518 | 12/1981 | Hattori et al. | 338/14 |
| 4,322,383 | 3/1982 | Yasuda et al. | 73/27 R |
| 4,327,054 | 4/1982 | Yasuda et al. | 73/27 R |

Primary Examiner—Daniel M. Yasich
Attorney, Agent, or Firm—Cushman, Darby & Cushman

[57]     ABSTRACT

A gas sensor having a gas sensing element of which electrical resistance changes in accordance with gas components contained in sensing gas and a ceramic member for firmly holding the sensing element is fixedly mounted, in which the gas components are detected by sensing a resistance of the gas sensing element. In the gas sensor, a conductive member which is mounted to the gas sensing element, extending through the center between a pair of lead members for sensing an electrical resistance of the gas sensing element, is provided on the ceramic member or the gas sensing element, and the conductive member is connected to ground.

4 Claims, 17 Drawing Figures

GAS SENSOR

The present invention relates to a gas sensor suitable for an exhaust gas cleaning system using a three way catalyzer for an automobile.

A gas sensor section of a conventional gas sensor has a construction as shown in FIGS. 1A to 1E. As shown, the gas sensor section is comprised of a pair of electrodes 2a, made of platinum, for sensing a change of an electrical resistance, due to a change of atmospheric gas, of a gas sensor element 1 which carries porous catalyzer in the form a metal oxide sintered body made of, such as titanium oxide etc. A rod-like ceramic body 3 carries the element 1 on one end and has a pair of throughholes 3a with the same diameters through which pass the electrode pair 2a of the gas sensor element 1. The tubular ceramic body 3 is provided with a groove 3c for holding the gas sensor element 1 and a groove 3b for leading exhaust gas to the gas sensor element 1, and further the gas sensor element 1 fitted therein, as shown in FIG. 1A.

It was found that when the above-mentioned gas sensor is exposed to exhaust gas, moisture, carbon, etc., in the exhaust gas, particularly at low temperature (300° C.), passes through a gap between the groove 3b of the ceramic body 3 and the gas sensor element 1 and attaches to the ceramic body 3 between the electrodes 2a. When those substances such as moisture and carbon attach to the ceramic body 3 as indicated by symbols X in FIG. 1D, a resistor formed by the deposit X is inserted across a resistor of the gas sensor element 1, with the result that an equivalent circuit shown in FIG. 1E is formed to provide a leak current between the electrode pair 2a of the gas sensor element 1. In FIG. 1E, Rs designates the resistor of the gas sensor element 1, Rc the resistor formed by the deposit and Rr a reference resistor. For example, the gas sensor element 1 exhibits one Mega ohms at a lean air-to-fuel (A/F) ratio 16 (oxidation side), and 30 Kilo ohms at a rich A/F ratio 13 (reduction side), at 300° C. of the exhaust gas temperature. When the resistance of the deposit X such as carbon is 100 Kilo ohms, and when the A/F is changed from lean to rich, the electrical resistance of the gas sensor element 1, which is given by $$\frac{R_C R_S}{R_C + R_S},$$

changes: 100 Kilo ohms ($\approx 100 \times 100000/100 + 100000$) at 16 of the A/F ratio and 23 Kilo ohms ($\approx 100 \times 30/100 + 30$) at 13 of the A/F ratio. As just mentioned, the resistance change in such a case is small and hence it is impossible to measure it.

Accordingly, the present invention has an object to provide a gas sensor which is able to sense an electrical resistance of the gas sensor element with relatively high correctness even if an electrical insulation between lead members for leading a resistance value of the gas sensor element is deteriorated due to the conductive deposit such as moisture and carbon.

As described above, during the course of gas sensing, conductive substances such as carbon and moisture adhere to the gas sensor particularly at low temperature. As a result, an apparent resistance of the gas sensing element decreases by the leak current through the deposit such as carbon, therefore, even when the atmosphere of the sensing gas changes from the oxidation to reduction side, a resistance change of the gas sensing element is small, which would otherwise be large. Therefore, it is impossible to sense the resistance change. On the other hand, in the present invention, a grounded conductive member is provided between the lead members of the gas sensing element, whereby the gas sensor according to the invention can measure resistance of the gas sensing element relatively correctly, being free from the adverse influence of the conductive deposit.

The present invention will better be understood when carefully reading the following description taken in connection with the accompanying drawings, in which.

Figure 1A:
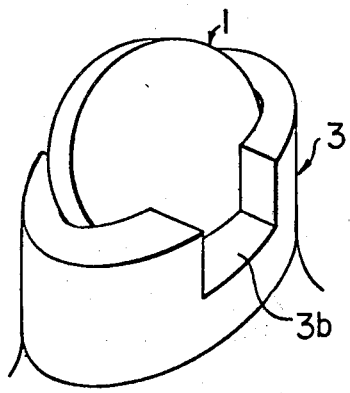
FIG. 1A is a perspective view of the combination of the ceramic member 3 and the gas sensing element 1 which is according to the prior art.
Figure 1B:
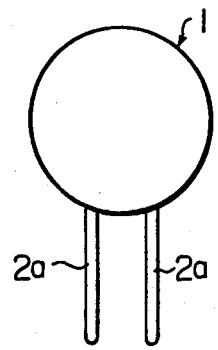
FIG. 1B is a front view of the gas sensing element.
Figure 1C:
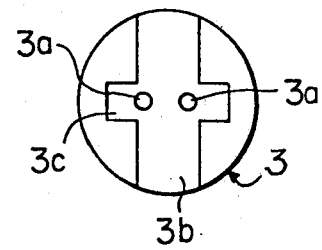
FIG. 1C is a bottom view of the ceramic body 3.
Figure 1D:
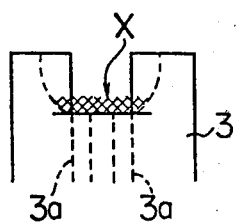
Figure 1E:
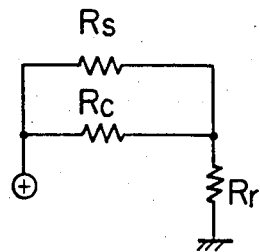
Figure 2A:
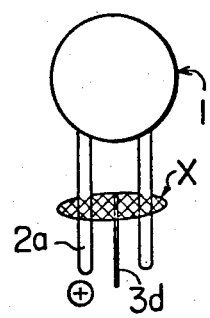
Figure 2B:
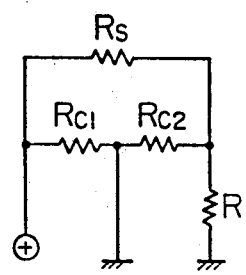
Figure 4:
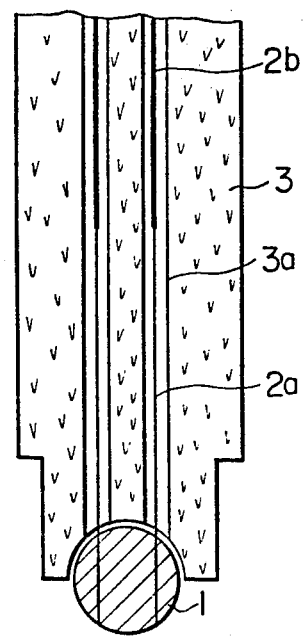
Figure 5A:
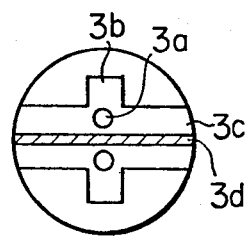
Figure 5B:
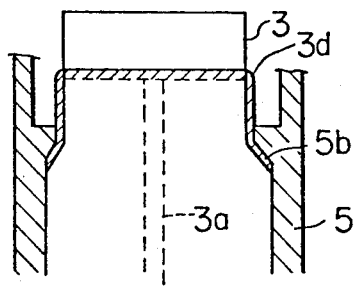
Figure 2C:
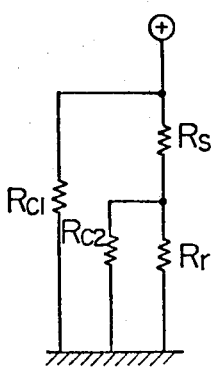
Figure 3:
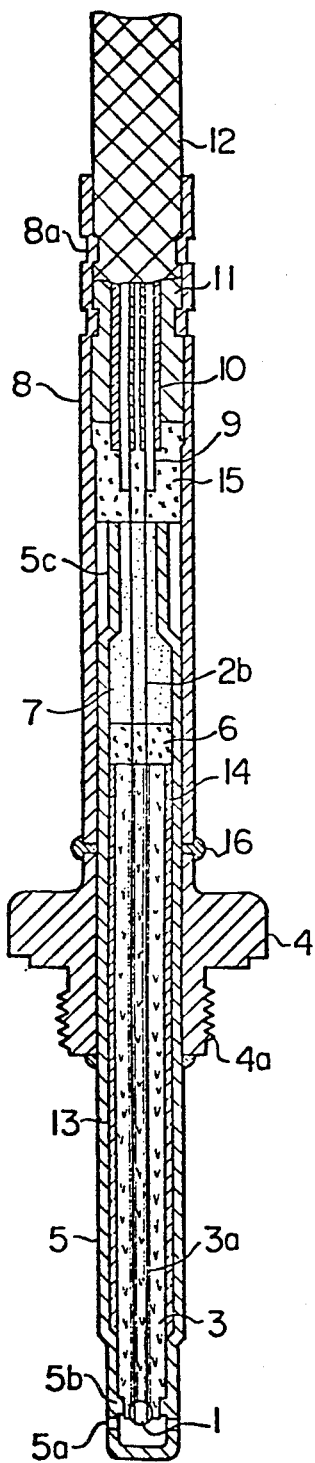
Figure 6A:
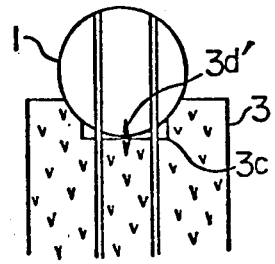
Figure 6C:
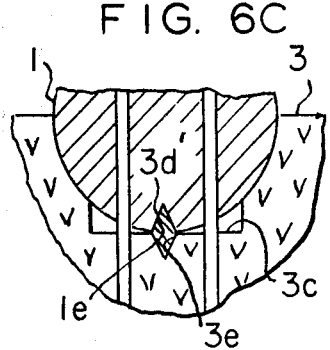
Figure 6B:
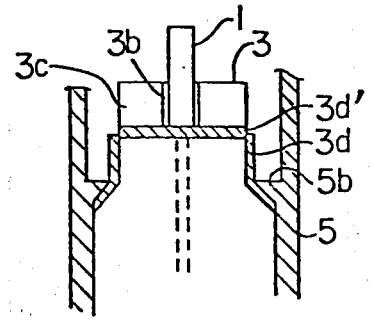
Figure 7A:
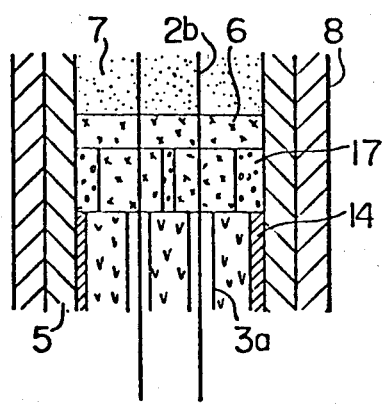
Figure 7B:
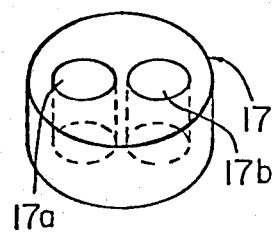

FIG. 1D diagramatically illustrates a state that conductive deposit such as carbon X attaches to the ceramic body 3;

FIG. 1E is an equivalent circuit of the gas sensor section when conductive deposit adhere to the ceramic body as shown in FIG. 1D;

FIG. 2A is a schematic diagram for illustrating the grounding of the conductive deposit which adversely affects the electrodes the gas sensing element section used in the present invention;

FIG. 2B is an equivalent circuit of the gas sensor shown in FIG. 2A;

FIG. 2C is an equivalent circuit which is the rearranged circuit shown in FIG. 2B;

FIG. 3 is a cross sectional view of an embodiment of a gas sensor according to the present invention;

FIG. 4 is an enlarged sectional view of a part of the gas sensor shown in FIG. 3;

FIG. 5A is an end view of the ceramic body 3 of the gas sensor shown in FIG. 3;

FIG. 5B is a sectional side elevation of a part including a pipe 5 of the gas sensor shown in FIG. 5A;

FIG. 6A is a cross sectional view a gas sensing element section of another embodiment of a gas sensor according to the present invention;

FIG. 6B is a sectional side elevation of a part including a pipe 5 of the gas sensor shown in FIG. 6A;

FIG. 6C is an enlarged view of a part of FIG. 6A;

FIG. 7A shows a cross sectional view of a major of yet another embodiment of a gas sensor according to the invention; and FIG. 7B is a perspective view of a ring member 17 of the gas sensor shown in FIG. 7A.

As shown in FIG. 2A, a conductive member 3d is provided in the midpoint of the deposit resistor Rc of the carbon X and is grounded. An equivalent circuit of the gas sensing element section shown in FIG. 2A is shown in FIG. 2B. With the provision of the conductive member 3d, a deposit resistor Rc₁ connected across the resistor Rs of the gas sensing element 1 is divided, so that a resistor Rc₁ ranging from a positive terminal of the gas sensing element 1 to the conductive member 3d is grounded, as shown. Further, a resistor Rc₂ from the conductive member 3d to a negative terminal of the gas sensing element is connected across the reference resistor Rr (FIG. 2C). Therefore, a parallel resistor across the resistor Rs of the gas sensing element 1 is eliminated, thus ensuring a correct measurement of the resistor Rs. In a practical use, the resistor Rc₂ coupled in parallel with the reference resistor Rs becomes problemmatic. However, the resistor $Rc_2$ has a resistance of 100 Kilo ohms, for example, for the reference resistor Rr of 100 Kilo ohms. Thus, those resistances are equal to each other and it has a negligible influence on an output voltage of the sensing element.

An embodiment of a gas sensor according to the present invention will be described referring to the accompanying drawings. FIG. 3 is a longitudinal sectional view of a first embodiment of a gas sensor according to the present invention. FIG. 4 illustrates a major portion of the embodiment shown in FIG. 3. FIG. 5 illustrates major portion of a ceramic body used in the embodiment shown in FIG. 3. Referring to FIGS. 3 to 5, a sensing element 1 of a metal oxide sintered body made of titanium or tin oxide, etc., which carries catalyzer. A pair of electrodes 2a made of platinum, for example, is buried in the sensing element 1. A pair of subleads 2b made of heat-resistive metal such as stainless is welded to the electrode pair 2a, the former thus being electrically connected to the latter. A tubular ceramic body 3 has a pair of thin throughholes 3a with the same diameters into which the electrode pair 2a and the sublead pair 2b are inserted. The tubular ceramic body 3 is made of heat-resistive and electrically insulated material such as alumina and has an expanded portion intermediate both ends thereof. Provided on the sensing element of the ceramic body 3 is a groove 3b for holding the sensing element 1 and another groove 3c allowing the exhaust gas to contact with the sensing element 1.

As shown in FIGS. 5A and 5B, a thin conductive member 3d passing through the center between the pair of the throughholes 3a is laid along the groove 3c. The conductive member 3d is formed by electron-beam depositing or past-baking metal with excellent heat- and corrosion-resistance such as platinum. The conductive member 3d extends along the side face of the ceramic body 3 and is electrically connected to a tubular pipe 5 for holding the ceramic body 3 at a contact portion 5b of it with the pipe 5. The pipe 5 is connected through a housing 4 to an exhaust pipe (not shown). The conductive member 3d is connected to ground (−) of a power source, via the housing 4 and the exhaust pipe. The pipe 5 is fixedly welded to the housing 4 and is made of heat- and corrosion-resistive metal. The pipe 5 is provided with an opening 5a for the exhaust gas passage. Inorganic gas sealing material 6, being in a solid state, fills a part of the pipe 5 so as to block the openings of the throughholes 3a. The glass sealing material 6 provides the sealing of the exhaust gas and the insulative-fixing of the subleads 2b. Powder 7 made of alumina or magnesium, etc., is used for fixing the subleads and for electrically insulating them. A heat-resistive metal pipe 8 is welded to the pipe 5. A pair of leads 9 are welded to the pair of subleads 2b, both being electrically connected. The leads 9 are covered with a cover 10 made of heat- and electrically insulative-material such as glass wool or heat-resistive rubber. The cover 10 is further covered with another cover 11 made of the same material, both being electrically insulated each other. A cover 12 which is a mesh of heat-resistive metal wires covers the outer surface of the cover 11. The cover 12 is fixed to the pipe 8 by caulking the end of the pipe 8 as indicated by 8a. The caulking of the end of the pipe 5 enhances a filling density of the internal electric insulating powder 7. Inorganic adhesive 13 such as Sumiceram (trade name), which is a product of the Sumitomo Chemical Co. Ltd., is injected and solidified in between the ceramic body 3 and pipe 5, thus both members being fixed rigidly. A heat-resistive metal ring 14 compresses the adhesive 13. Heat-resistive rubber 15 such as silicon rubber is disposed between the pipe 5 and the outermost cover 12 of the lead 9 within the pipe 8. The pipe 8 and the housing 4 are welded and fixedly connected to each other at a portion denoted as 16.

With an arrangement as mentioned above, one of the pair of the leads 9 is connected to the (+) side of the power source, while the other is connected to the (−) side of the power source, through the reference resistor and a control circuit which provides, in response to changes of the air-to-fuel ratio sensed by the gas sensor element, control signals for modulating air-to-fuel ratio of the combustion mixture to be provided to an internal combustion engine. The control circuit corresponds to the electrical circuit shown in FIG. 4 of U.S. Pat. No. 3,959,765. An equivalent circuit of the gas sensor is as illustrated in FIG. 2C. In the figure, the control circuit is eliminated for simplicity. Alternately, a lead may be connected to the conductive member 3d and to ground.

Turning now to FIGS. 6A, 6B and 6C there is shown another embodiment of a gas sensor according to the present invention, although only a major part thereof is illustrated. In the figure, V grooves 3e and 1e are formed between the electrodes 2a and 2b in a groove 3c of the ceramic body and the gas sensing element 1. A V-shaped metal plate 3d' made of heat- and corrosion-resistive material such as stainless is fitted into the respective V grooves. Both ends of the metal plate 3d' are electrically connected to the conductive member 3d made of platinum, for example, provided on the side face of the ceramic body 3 by the past-baking. Further, the conductive member 3d is electrically connected to the pipe 5. In this embodiment, there arises no problem even when conductive substances such as carbon are attached to the gas sensing element 1.

FIGS. 7A and 7B illustrate yet another embodiment of a gas sensor according to the present invention. In the present embodiment, a ring member 17, made of heat- and corrosion-resistive material such as stainless, with two holes 17a and 17b is inserted in the glass seal material 6 shown in FIG. 3. The ring member 17 is electrically connected at the periphery to the pipe 5. According to the present embodiment, the gas sensor of the present embodiment has no problem even when the electrical insulation between the subleads 2b is deteriorated by a quality change of the glass seal material contained in the exhaust gas when the exhaust gas reaches the glass seal material 6, through the throughholes 3a of the ceramic body 3.

What is claimed is:

1. A gas sensor comprising: a gas sensing element of which electrical resistance changes in accordance with gas components contained in sensing gas; a pair of lead members attached to said gas sensing element for reading an electrical resistance of said gas sensing element; a ceramic member in a tubular metallic body that is connected to ground, said gas sensing element being held at one end of said ceramic member which has a pair of throughholes for allowing said pair of lead members to pass therethrough; and a conductive member provided at said one end of said ceramic member and near said gas sensing element between the pair of said lead members, said conductive member being connected to ground, whereby when a deposit of conductive material builds up on said one end of said ceramic member and across said pair of lead members, the electrical resistance of said gas sensing element can be measured correctly.

2. A gas sensor according to claim 1, wherein said ceramic member has a groove leading sensing gas to said gas sensing element, and said conductive member passes between said throughholes along said groove.

3. A gas sensor according to claim 1, wherein opposed V-shaped grooves are provided between said lead pair on said gas sensing element and on said one end of said ceramic member, and a metal plate is fitted in said V-shaped grooves as a conductor disposed between said lead members and is grounded to said metallic body.

4. A gas sensor according to claim 1, wherein a heat- and corrosion-resistive ring member with two holes is placed in a sealing member provided at the other end of said ceramic member remote from said sensing element, through which holes the pair of said lead members led from said gas sensor element extend, the periphery of said ring member being grounded.

* * * * *